(12) United States Patent
Hendrix (10) Patent No.: US 11,443,840 B1
(45) Date of Patent: *Sep. 13, 2022

(54) MEDICATION ADHERENCE APPARATUS

(71) Applicant: GuardianMedTech, LLC, Oldsmar, FL (US)

(72) Inventor: Anna Noel Hendrix, Palm Harbor, FL (US)

(73) Assignee: Guardianmedtech, LLC, Oldsmar, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/231,765

(22) Filed: Apr. 15, 2021

Related U.S. Application Data (63) Continuation of application No. 17/074,927, filed on Oct. 20, 2020, now Pat. No. 11,017,893, which is a continuation of application No. 16/558,746, filed on Sep. 3, 2019, now Pat. No. 10,825,559.

(51) Int. Cl.
| | |
|---|---|
| *G16H 20/10* | (2018.01) |
| *G06K 7/14* | (2006.01) |
| *A61J 1/03* | (2006.01) |
| *A61J 7/04* | (2006.01) |

(52) U.S. Cl.
CPC ............ *G16H 20/10* (2018.01); *A61J 1/03* (2013.01); *A61J 7/04* (2013.01); *G06K 7/1417* (2013.01); *A61J 2200/30* (2013.01); *A61J 2205/10* (2013.01)

(58) Field of Classification Search
CPC ......... G16H 20/10; G06K 7/1417; A61J 1/03; A61J 7/04; A61J 2205/10; A61J 2200/30
See application file for complete search history.

(56) References Cited

U.S. PATENT DOCUMENTS

| | | | |
|---|---|---|---|
| 6,529,446 B1 | 3/2003 | de la Huerga | |
| 7,705,734 B2 * | 4/2010 | Martinelli | G06Q 10/08 215/202 |
| 10,740,440 B2 * | 8/2020 | Woodyear | G16H 20/10 |
| 10,751,259 B1 * | 8/2020 | Dutta | A61J 7/0436 |
| 10,825,559 B1 * | 11/2020 | Hopen | G06K 7/1417 |
| 11,017,893 B2 * | 5/2021 | Hopen | G16H 40/67 |

(Continued)

OTHER PUBLICATIONS

Bennadi D. (2013). Self-medication: A current challenge. Journal of Basic and Clinical Pharmacy, 5(1), 19-23.

(Continued)

*Primary Examiner* — Michael Collins
(74) *Attorney, Agent, or Firm* — Anton J. Hopen; Smith & Hopen, P. A.

(57) ABSTRACT

A medication container for validating self-administration of prescription medication by a patient wherein the prescription medication is administered over a series of timed dosages. A machine-readable optical code label such as a QR Code is affixed to an interior surface of a medication container containing the medication such as the interior of the bottle cap. The container must be open to electronically read the optical code label. The label contains data associated with the medication and is read by a software application installed on a smartphone. The software receives the label-embedded data and a timestamp to validate the patient is self-administering the medication consistent with the series of timed dosages.

19 Claims, 13 Drawing Sheets

(56) References Cited

U.S. PATENT DOCUMENTS

| | | | |
|---|---|---|---|
| 11,152,093 B1* | 10/2021 | Hopen, Sr. | G16H 10/20 |
| 2008/0027291 A1 | 1/2008 | Williams-Hartman | |
| 2014/0188502 A1* | 7/2014 | Defrank | G16H 40/67 |
| | | | 705/2 |
| 2014/0364202 A1* | 12/2014 | Harms | A63F 13/69 |
| | | | 463/29 |
| 2017/0349343 A1* | 12/2017 | Wu | B65D 55/02 |
| 2021/0001061 A1* | 1/2021 | Calderon Oliveras | A61M 15/0065 |

OTHER PUBLICATIONS

Michael, C. A., Dominey-Howes, D., & Labbate, M. (2014). The antimicrobial resistance crisis: causes, consequences, and management. Frontiers in Public Dealth, 2, 145.

Rather, I. A., Kim, B. C., Bajpai, V. K., & Park, Y. H. (2017). Self-medication and antibiotic resistance: Crisis, current challenges, and prevention. Saudi Journal of Biological Sciences, 24(4), 808-812.

* cited by examiner

Fig. 1

Prior Art

Fig. 2

Prior Art

MEDICATION ADHERENCE APPARATUS

CROSS REFERENCE TO RELATED APPLICATIONS

This application is a continuation of and claims priority to U.S. Non-Provisional patent application Ser. No. 17/074,927 entitled "Medication Container for Dosage Compliance" filed Oct. 20, 2020, which is a continuation of and claims priority to U.S. Non-Provisional patent application Ser. No. 16/558,746 entitled "Interiorly Positioned Machine-Readable Data Labels for Prescription Compliance", filed on Oct. 3, 2019 (now U.S. Pat. No. 10,825,559).

BACKGROUND OF THE INVENTION

1. Field of the Invention

This invention relates to a medication container to improve patient compliance with a medication regiment.

2. Brief Description of the Related Art

Lack of compliance with scheduled dosage of prescribed medicine has significantly detrimental consequences to both individual patients and public health. Lack of compliance to antibiotic treatment courses and improper self-medication are major reasons for the increase in drug-induced diseases and development of antibiotic resistance crisis. Bennadi D. (2013). *Self-medication: A current challenge.* Journal of Basic and Clinical Pharmacy, 5(1), 19-23. doi:10.4103/0976-0105.128253. Self-medication is the most common reason for the development of human pathogen resistance to antibiotic drugs. Michael, C. A., Dominey-Howes, D., & Labbate, M. (2014). *The antimicrobial resistance crisis: causes, consequences, and management.* Frontiers in Public Dealth, 2, 145. doi:10.3389/fpubh.2014.00145. The general public's involvement as an active contributor to antibiotic resistance crisis needs to be solved through proper awareness initiatives. Rather, I. A., Kim, B. C., Bajpai, V. K., & Park, Y. H. (2017). *Self-medication and antibiotic resistance: Crisis, current challenges, and prevention.* Saudi Journal of Biological Sciences, 24(4), 808-812. doi:10.1016/j.sjbs.2017.01.004

Increasing compliance with self-medication has several advantages including effective treatment of illnesses and lower rates of re-admission. Long-term benefits include, but are not limited to, greater autonomy for patients receiving tuberculosis treatment, establishing electronic records of recently taken medications for emergency personnel and early warning for potential drug interactions.

What is needed in the art is a simple, inexpensive way to validate and monitor a patient's compliance to a dosage schedule and full completion of a course of prescribed medication.

BRIEF SUMMARY OF THE INVENTION

The present invention is a method and system of validating self-administration of prescription medication by a patient. Specifically, the prescription medication is administrable over a series of timed dosages (for example, taking three capsules per day over 10 days).

An embodiment of the invention includes affixing a machine-readable optical code label on an interior surface of a prescription medication container containing the prescribed medication. Imprinting of the label may be performed onto an adhesive label which is affixed to the interior surface of the prescription medication container. The machine-readable optical code label may include a format that contains sufficient data capacity to be useful. Embodiments of the invention place the optical code label on the interior face of the bottle cap, the interior bottom surface of the bottle and the interior surfaces of the bottle's cylindrical sidewalls. Each placement has certain advantages. For example, placing the label on the cap forgoes any visual occlusion by remaining pills or capsules in the bottle. However, if the patient is taking multiple prescriptions, and opens multiple bottles simultaneously, then the wrong cap may be put back on the wrong bottle. Putting the label on the bottom of the container would typically only be useful for an application that confirms all medicine has been consumed (e.g., an empty bottle). Placing the label on the upper, interior, sidewall surface of the bottle may be advantageous as the label remains associated with the vessel containing the medicine and is independent of caps being interchanged between bottles. It would also be viewable in most circumstances even with substantial amounts of medicine remaining in the bottle. Various types of machine-readable optical labels are still readable even if there is a partial occlusion of the label.

For example, a UPC-A barcode may contain an integer associated with a primary key that, in turn, links to a specific prescription. However, a two-dimensional matrix may contain far more information including the alphanumeric data specific to the prescription including the patient name, prescribing provider, prescription date, dosage instructions, side-effect warnings and the like. Matrix labels may include those as AZTEC CODE (International Standard: ISO/IEC 24778), DATA MATRIX (International Standard: ISO/IEC 16022), DOTCODE (Standardized as AIM Dotcode Rev 3.0.), MAXICODE, QR CODE (International Standard: ISO/IEC 18004), and the like. For the purpose of this disclosure, a terse prescription may be conveyed in 50 characters which would require a 33×33 QR Code. However, for most embodiments of the invention to convey full prescription data without requiring a round-trip to an external server, a QR Code Version 10 (57×57) conveying 174 characters with error-correction using the Reed-Solomon error correction algorithm should be sufficient.

An embodiment of the invention organizes the prescription information into structured data fields so that string and numeric values have context. This permits the software application on a mobile device to scan the optical label and interpret the structured data to organize a dosage schedule within the software application on the mobile device. An advantage of this approach is that the software application does not need access to third party network resources (such as RESTful APIs or web services) to function. By obviating the necessity of these communications, the implementation of this invention is much easier and efficient. Furthermore, sending and retrieving sensitive health information requires additional layers of security and legal compliance. Because all the same information exists in the optical label that exists on the human-readable outside label of the bottle or container, there are no additional security concerns. While mark up languages liked XML can store data they can be relatively verbose. Accordingly, fixed width and delimited data formats may be used to convey the most characters using less data-dense optical label formats.

Mishandling of prescription medications stems from may circumstances including, but not limited to, forgetfulness, losing the medication, taking the wrong medication out of multiple prescriptions, and willful abandonment of completing the prescribed course of medication. One tenant of the present invention is that proper administration of the medication is far more likely if the patient has the medication in front of them and the container open. One objective of the present invention is to induce and verify that the patient has the medication present and available at the right time consistent with their dosage schedule.

Accordingly, the container must be open to electronically read the optical code label. The optical code label contains the label-embedded data associated with the prescription medication and readable by a software application installed on a portable electronic device such as a smartphone. The software application receives the label-embedded data and a timestamp to validate the patient is self-administering the prescription medication consistent with the series of timed dosages and automatically generates an alert notification to a healthcare administrator responsive to a deviation in the series of timed dosages.

The software application can require various levels of interaction with the patient. On one end of the spectrum, the patient simply initiates the application and points the mobile device in the direction of the optical code label. The software application reads the data from the label and confirms a timestamp from the internal clock of the mobile device. No other interaction is required by the user. Alternatively, embodiments of the invention may show graphic representations of the medication (e.g., pill or capsule) on the screen of the mobile device so that the patient has visual confirmation he or she is consuming the correct medication (the graphic may include the prescribed medication imprint). Data embedded in the label may include telephone or other contact data for the prescribing healthcare provider. Accordingly, the mobile device software, reading the optical label, may automatically generate links and pathways to the healthcare provider without having a separate datastore or configuration process. For example, the healthcare provider may set aside an email address or web service to receive a message or post message each time the patient scans the label. Since the label already has the patient and healthcare provide information embedded, the process may be automatically handled directly from the mobile device with minimal or no proxy systems in between. Yet another advantage of the present invention is that a "confidential" email or web service URI may be specified in the QR Code but not human-readable. This avoids unnecessary or unintended email or web traffic to designated reception points. For example, an email address may be designed <dosagevalidation444@domain.com> which receives structured emails for the patients of the health care provider that confirm they are taking their medications according to this invention.

The location of the label can be placed at one or more locations in the medication container. A typical prescription medication container has a cylindrical body having a closed bottom and an open top and a cap threadably receivable to the open top of the body. The cap is affixed to the open top of the body to secure the medicine inside the container. The cap has an exterior surface facing away from the body when the cap and body are engaged and an interior surface facing the interior of the body when the cap and body are engaged.

In one embodiment of the invention, the optical code label is affixed to the interior surface of the cap. In another embodiment of the invention, the optical code label is affixed to the interior surface of the closed bottom of the cylindrical body. In yet another embodiment of the invention, labels may be placed at both locations wherein the optical code label at the closed bottom of the cylindrical body includes embedded data conveying its position in the prescription medication container whereby scanning of the label is associated with completion of the series of timed dosages because there is no medicine left in the container to occlude the imaging of that label.

The software application installed on the mobile device may read the label-embedded data and generate patient reminders on the mobile device system corresponding with the series of timed dosages.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
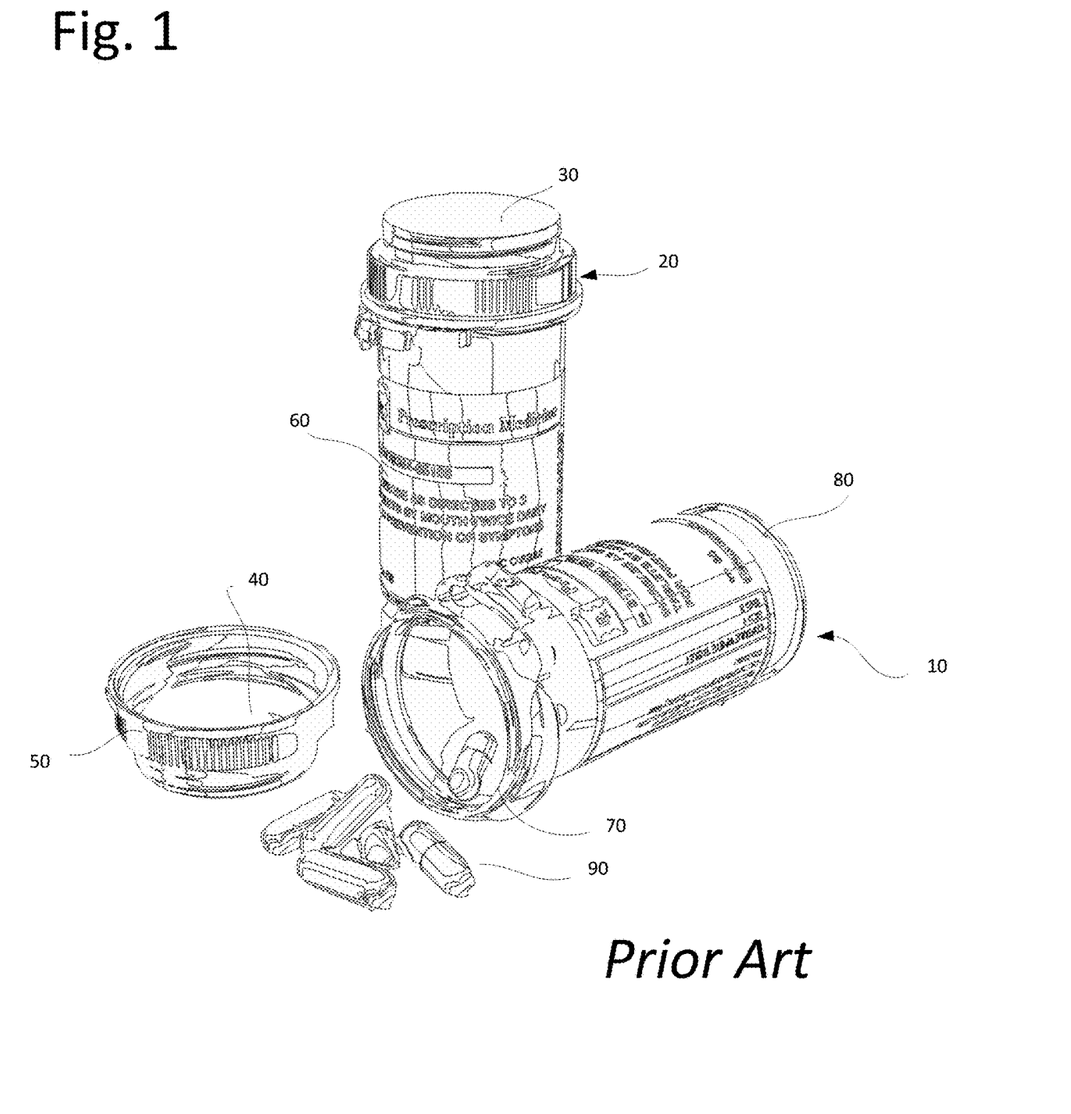
FIG. 1 is an perspective, photo-realistic view of a common prescription container known in the art.
Figure 2:
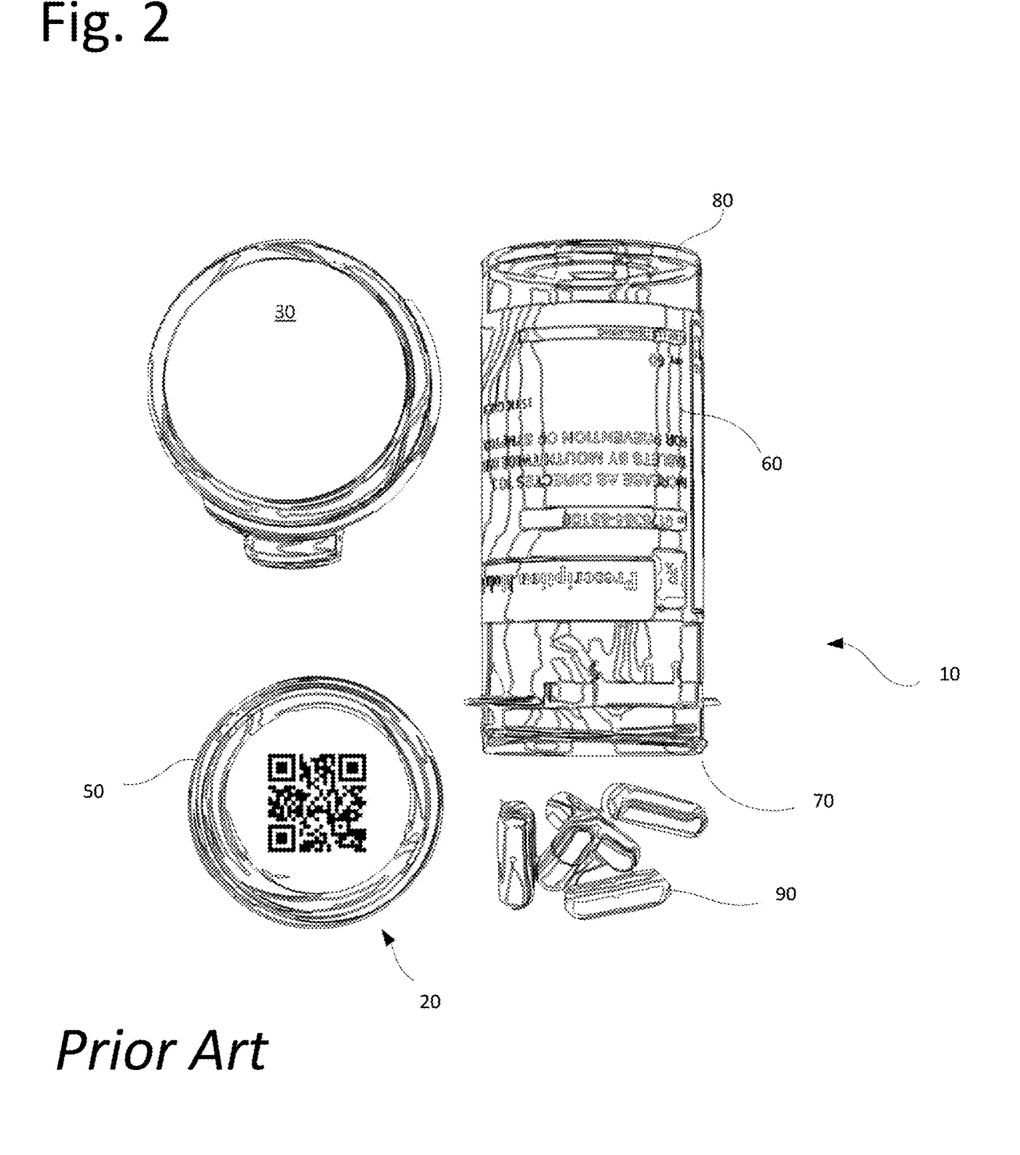
FIG. 2 is a top-down, photo-realistic view of a common prescription container known in the art.

Turning now to FIGS. 1 and 2 (both prior art) a typical pill bottle 10 is shown having a cylindrical bottom 80, a cylindrical opening 70 that holds medicine 90. A cap 20 is usually threadably received by opening 70. Cap 20 has an exterior top 30, cap sidewall 50 and cap interior surface 40. Prescription label 60 is affixed to the bottle cylinder sidewall. Affixing a machine-readable label (bar code, QR code, etc. . . . ) on label 60 may be useful in certain applications but it does not require the patient to actually open the bottle 10. Accordingly, it is insufficient to simply validate that the bottle 10 is in possession of the patient. The present invention requires the patient to remove cap 20 from bottle 10 which in turn makes medicine 90 readably accessible and more likely to be ingested.

Figure 3:
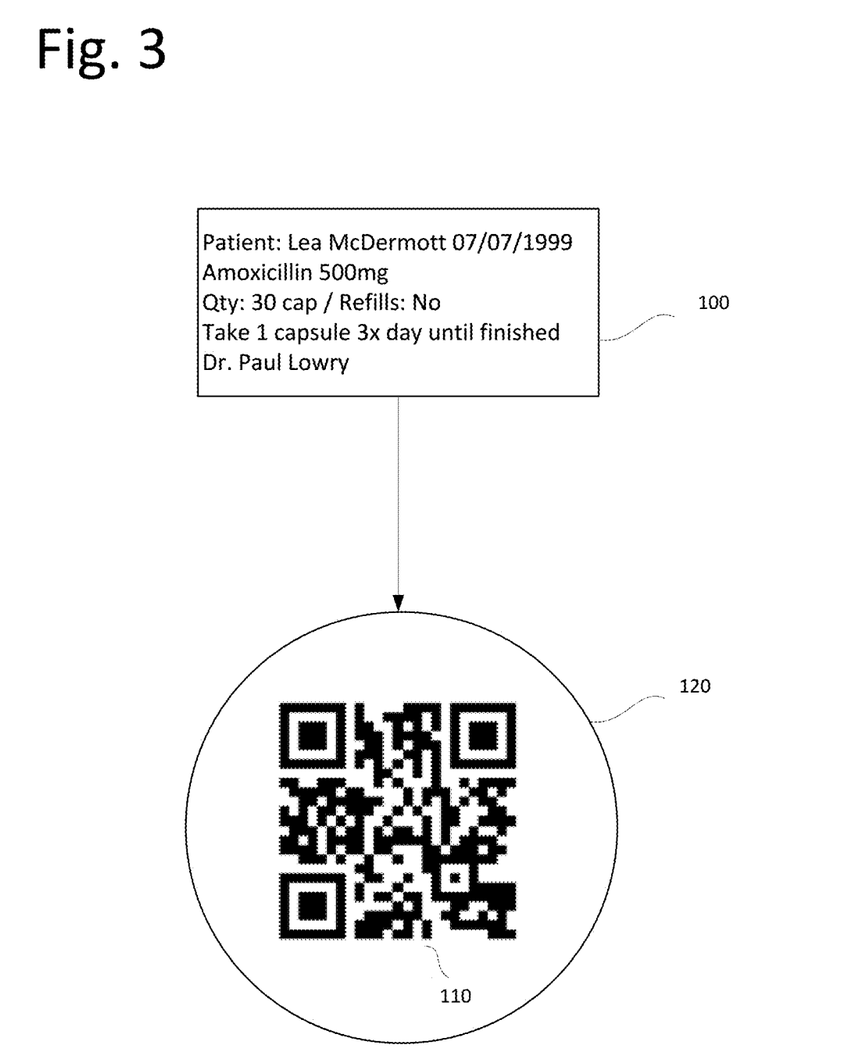
FIG. 3 is a diagrammatic view of a text-based prescription converted to a machine-readable optical label.

FIG. 3 shows a diagrammatic view of text string 100 comprising a prescription converted to a QR Code 110 on a circular adhesive label 120. Text string 100 is collectively 125 characters including white spaces so the QR Code 110 is illustrative only. The appropriate density and capacity of the machine-readable label may be adjusted as needed.

Figure 4:
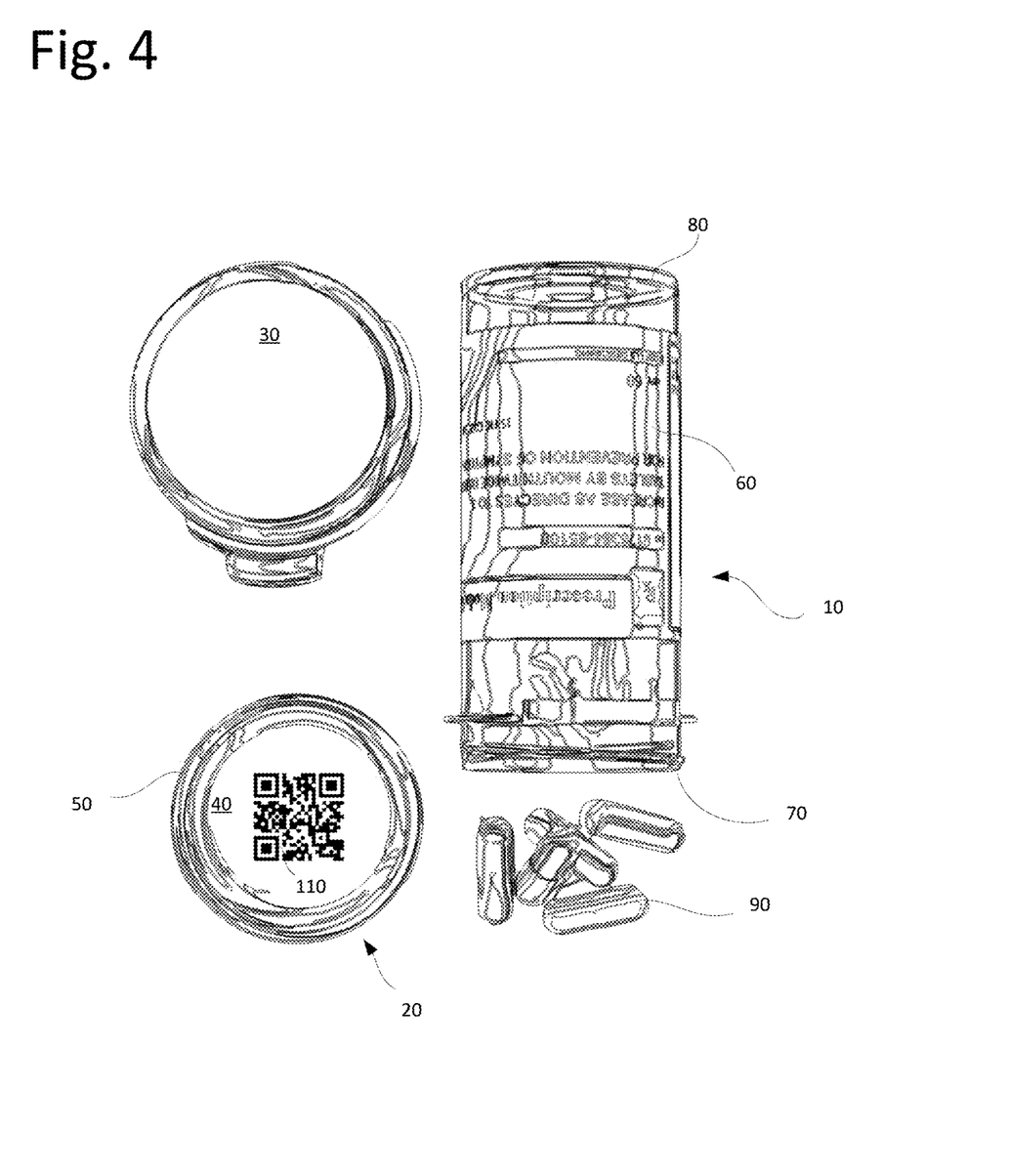
FIG. 4 is a top-down, photo-realistic view of an embodiment of the invention.
Figure 5:
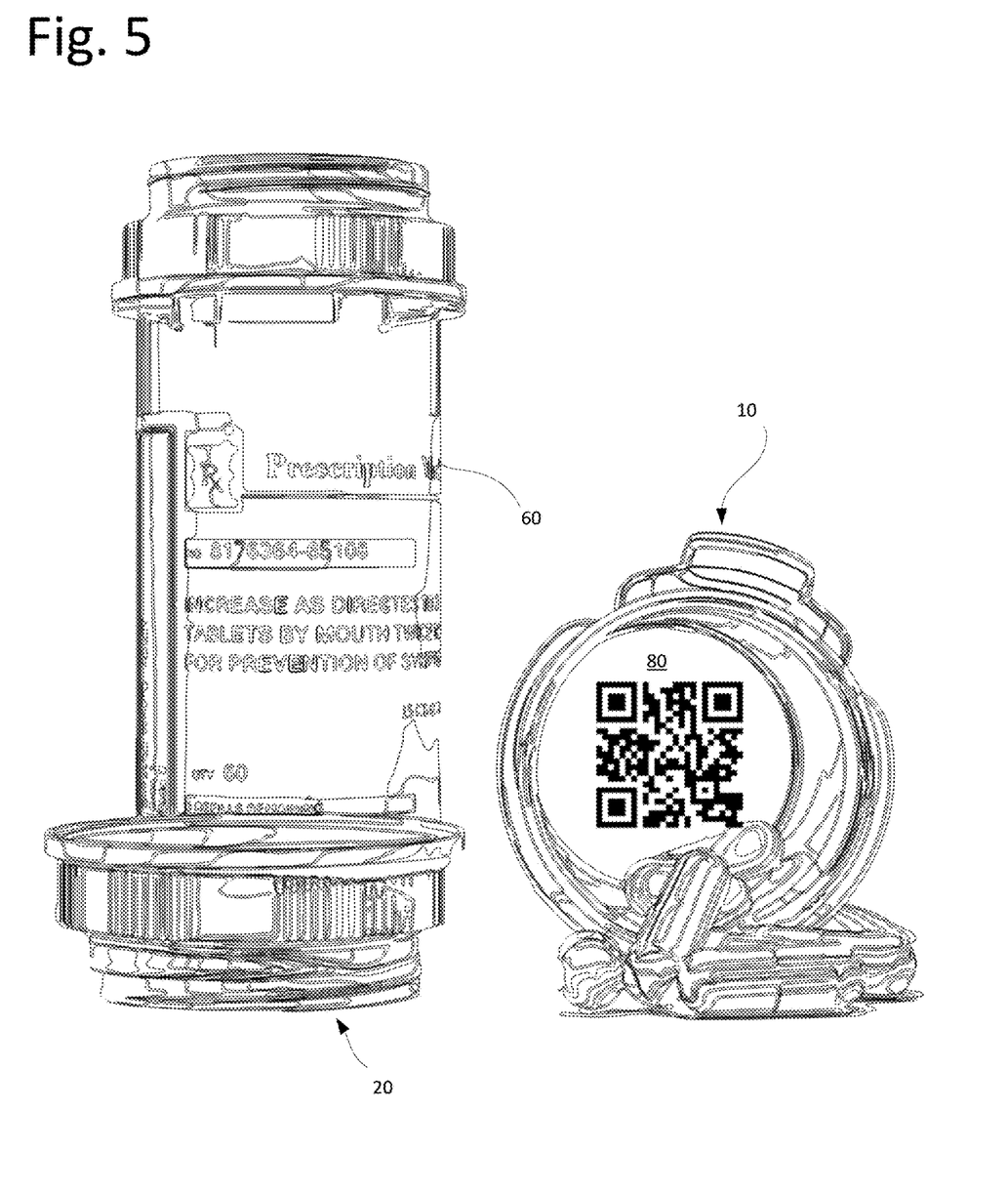
FIG. 5 is a front elevation, photo-realistic view of an alternative embodiment of the invention.

In the embodiment shown in FIG. 4, QR Code 110 is affixed to cap interior surface 40. Accordingly, the label otherwise obscured or occluded when cap 20 is threaded onto the bottle 10. Therefore, to operate the invention, the patient must remove cap 20 from bottle 10 thereby making medicine readily accessible. FIG. 5 shows an alternative embodiment of the invention wherein label 110 is affixed to cylindrical bottom 80. This position may be used in isolation or in conjunction with another label cap affixed to cap interior surface 40. When label 110 is affixed to cylindrical bottom 80, it is generally only readable once medicine 90 has been either removed or fully consumed. Accordingly, for some applications, it may be only necessary to verify that all medicine 90 has been consumed by patient so only one reading of label 110 affixed to cylindrical bottom 80 is necessary.

Figure 6:
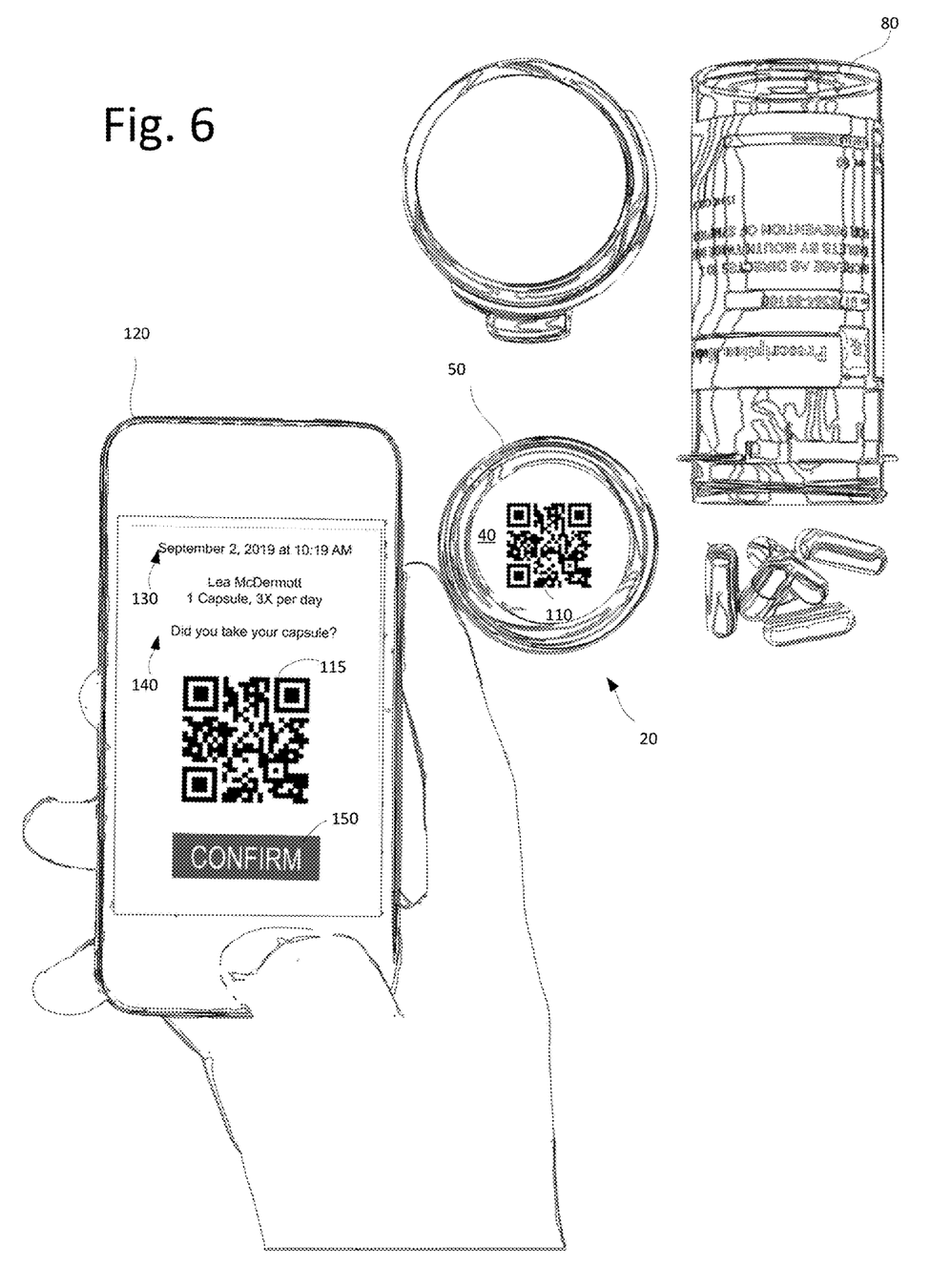
FIG. 6 is a top-down, photo-realistic view of an embodiment of the invention wherein a mobile device reads the optical label and queries the patient to confirm they have taken a dosage.

FIG. 6 shows an example of a smartphone 120 reading label 110 and reproducing it on the user interface (UI) as label 115. Because the string content 100 is embedded in label 110, the software application running on smartphone 120 extracts the strings and presents the information on the UI. The internal clock in the smartphone 120 establishes a timestamp 130 of the reading of the label 110 and the UI prompts 140 the patient to engage confirmation button 150 indicating they have ingested medication 90. An alternative embodiment of the invention may skip the confirmation button 150 and simply assume the patient has taken medication immediately upon reading label 110.

Figure 7:
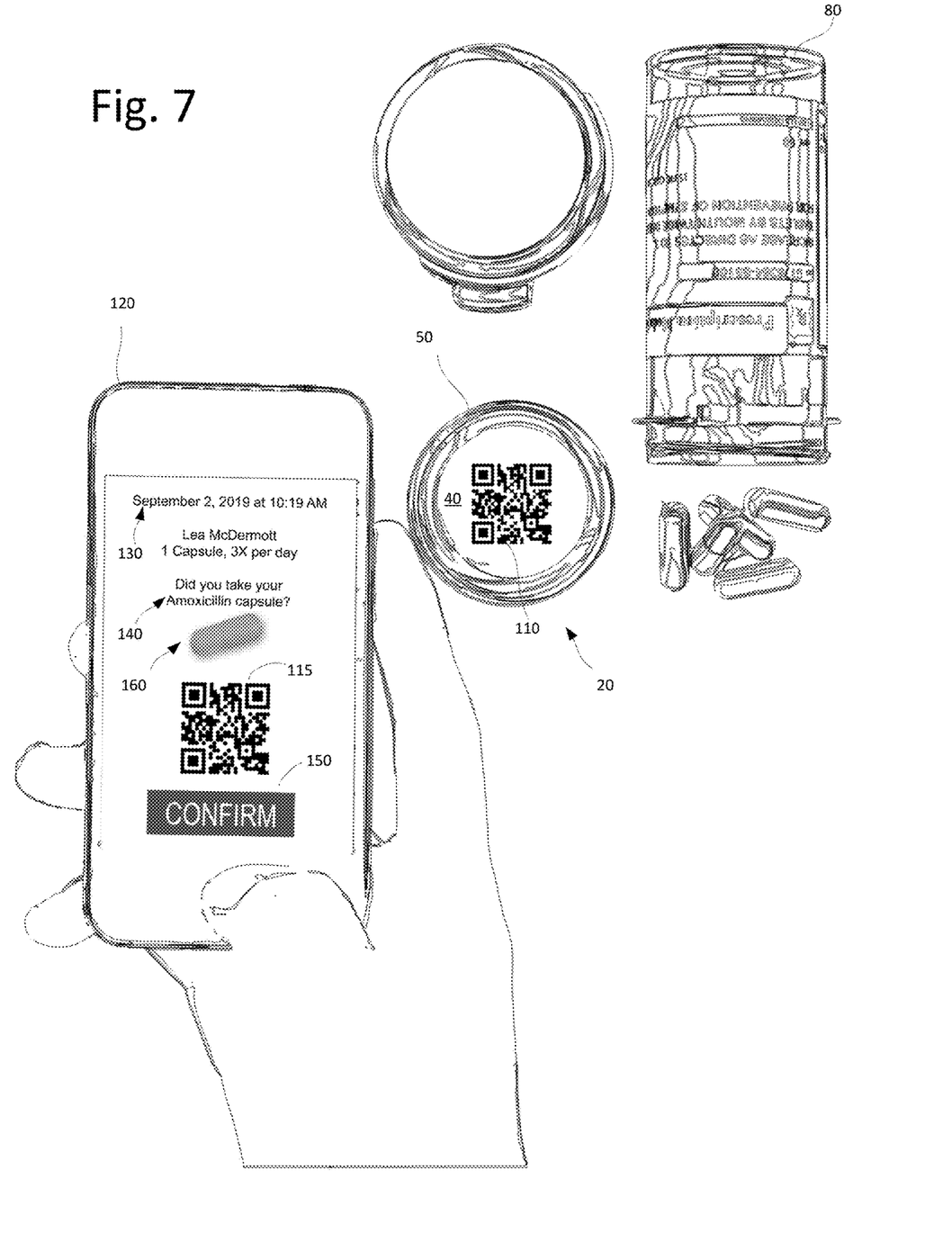
FIG. 7 is a top-down, photo-realistic view of an alternative embodiment of the invention wherein a mobile device reads the optical label, requests confirmation from the patient and also presents an image of the medication to be consumed.
Figure 8:
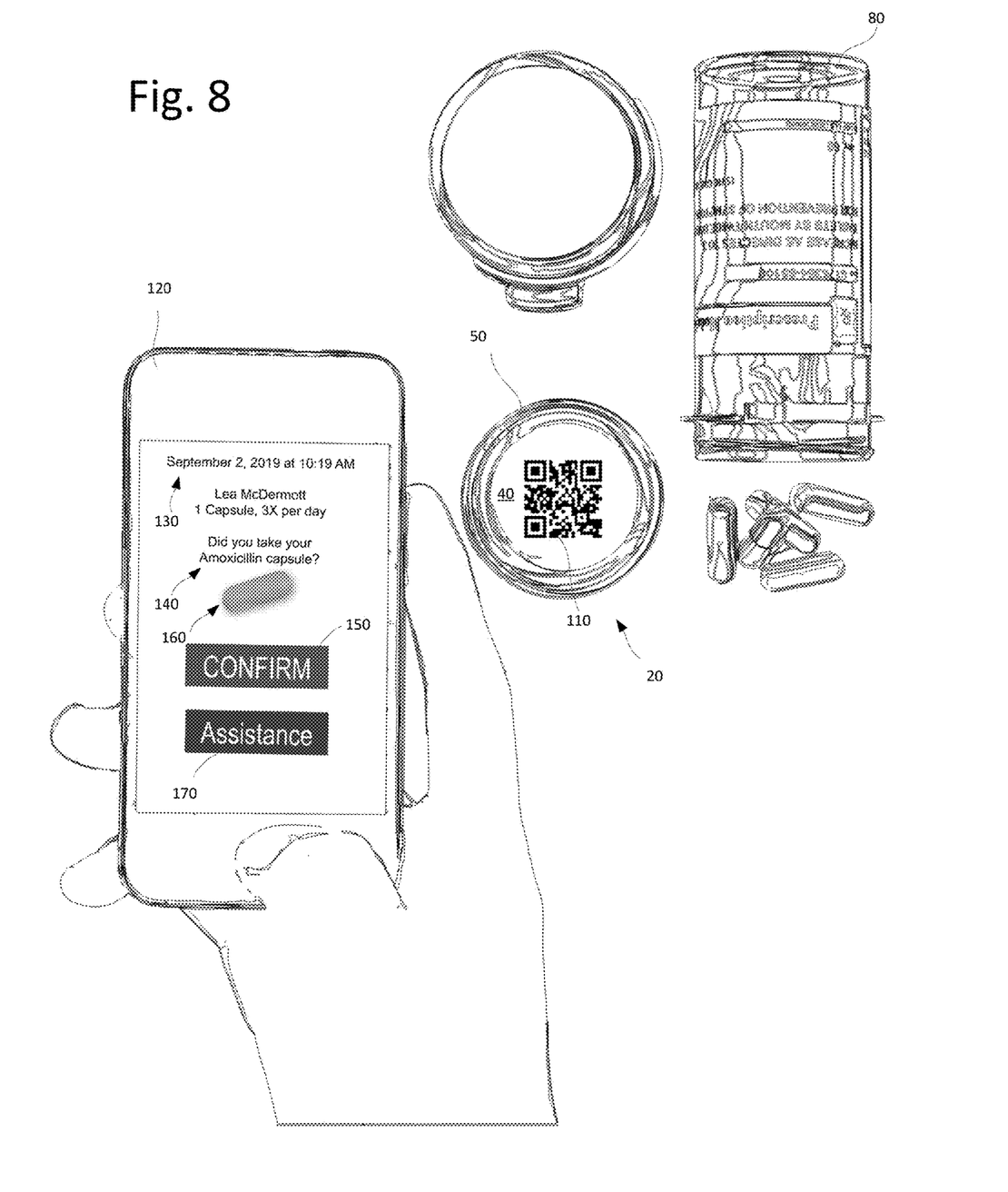
FIG. 8 is a top-down, photo-realistic view of an alternative embodiment of the invention wherein a mobile device provides a patient option to request assistance.

FIG. 7 shows an embodiment of the invention displaying capsule 160 on the UI of smartphone 120 wherein patient has additional visual verification they are consuming the correction medication 90. FIG. 8 shows an embodiment that includes an assistance link 170 which may fire an event that includes calling the prescribing healthcare provider, the pharmacy, a designated third-party healthcare professional, or a trusted family member. The phone number may be embedded into the label 110 wherein is it not otherwise human-readable. The assistance link 170 may also initiate a telemedicine session, an email, a chat application or a request for a call back to the patient. The assistance link 170 may also be a URL value that opens a web page or application containing information on side effects, recommendations on how to take medicine 90 or other information to assist the patient.

Figure 9:
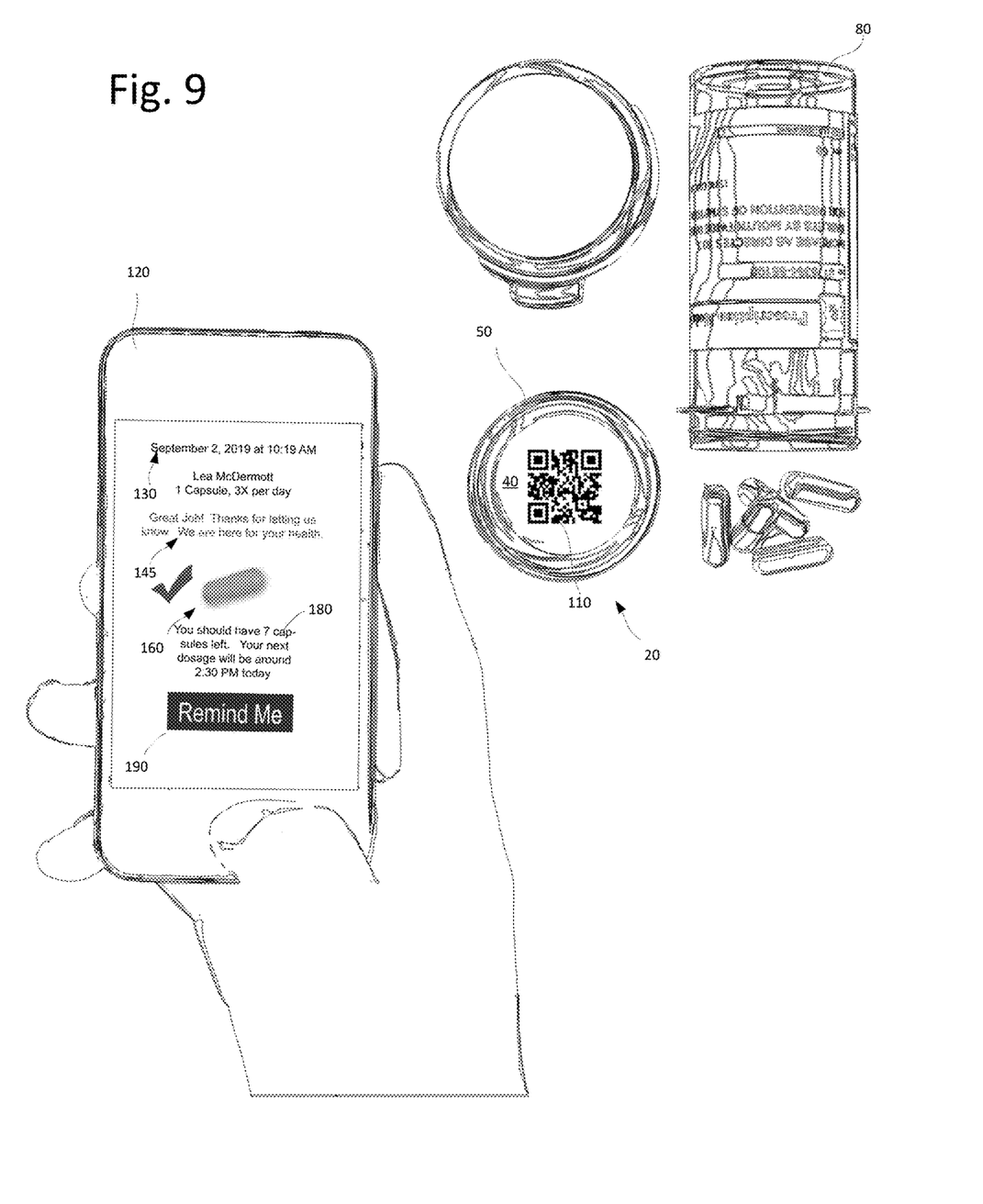
FIG. 9 is a top-down, photo-realistic view of an alternative embodiment of the invention wherein a mobile device responds to confirmation by the patient and offers to generate a scheduled reminder for the next dosage.

FIG. 9 shows an embodiment of the UI of the smartphone 120 after patient has confirmed taking the schedule dosage. In the example, show, the patient is to take 1 capsule three times per day. The timestamp 130 indicate the dosage was just taken at 10:19 AM. Accordingly, the software application running on smartphone 120 calculates the next dosage should be at approximately 2:30 PM and prompts 190 the patient whether they want a reminder on smartphone 120 at that time.

Figure 10:
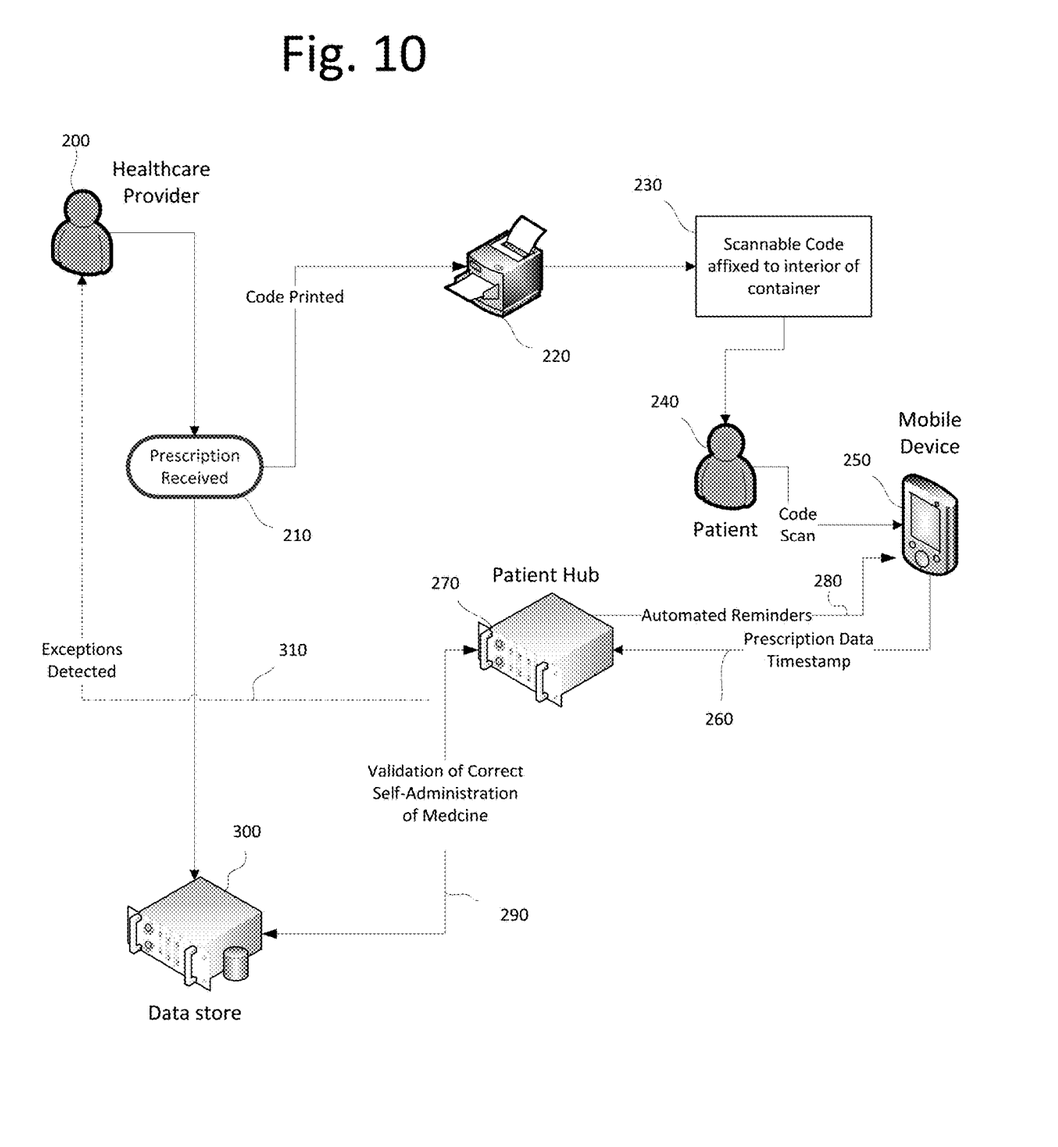
FIG. 10 is a process view of a method of implementing an embodiment of the invention.

FIG. 10 shows a workflow according to an embodiment of the invention wherein healthcare provider 200 sends a prescription to pharmacy 210. Prescription data is also sent to data store 300 which include the date of prescription and dosage schedule. Pharmacy 210 prints a machine-readable label 220 and affixes 230 to the interior of the container of medicine. The container is delivered to patient 240 who then uses mobile device 250 to scan label 220. The prescription data embedded in label 220 along with the timestamp of the scan 260 is sent to patient hub 270. Patient hub 270 validates 290 the correct self-administration of medicine by patient 240 against the prescription records in data store 300. If patient 240 scans label 220 too many times or not a sufficient number of times, an exception 310 is detected and an alert is generated back to healthcare provider 200.

Figure 11:
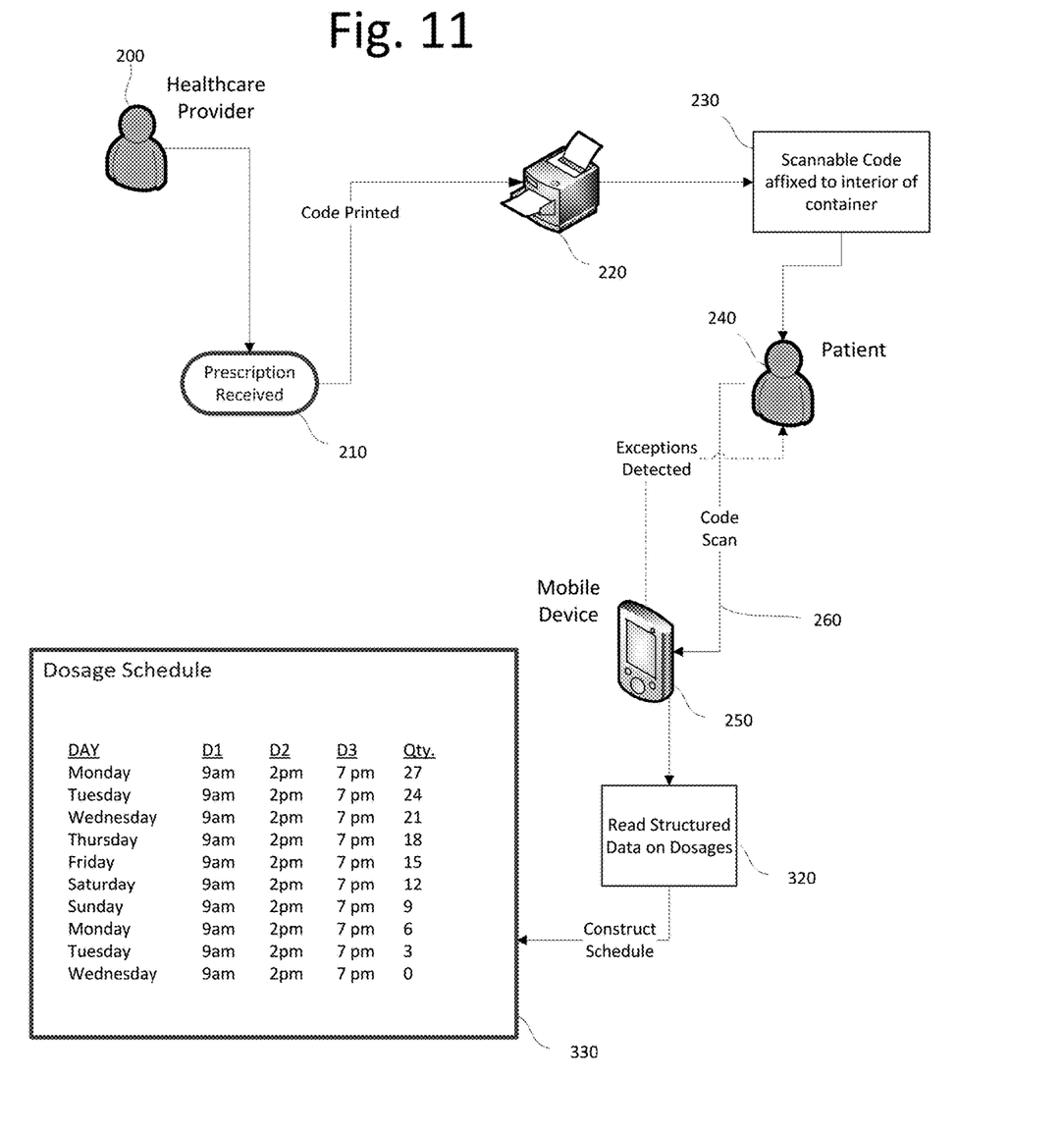
FIG. 11 is a process view of a method of implementing an embodiment of the invention wherein structured data embedded in the optical label builds a dosage schedule on the mobile device software.

FIG. 11 shows an alternative embodiment of the invention wherein the first time 320 the mobile device reads the optical label a dosage schedule 330 is generated. This is feasible when the alphanumeric characters convey each field in context such as with fixed-width, delimited or tagged (e.g., XML) strings. When the strings from the optical label are parsed by the mobile device, the mobile device in this embodiment has all the necessary information to create a dosage schedule without calling out to external network resources such as a web service. Accordingly, this provides assurance that the application will function when the patient is traveling, is out of an Internet service area or there is a network disruption. In the example in FIG. 11, thirty capsules are to be taken over 10 days, three capsules a day. The dosage schedule 330 is constructed. The dosage schedule 330 may be integrated into third party applications such as MICROSOFT OUTLOOK or GOOGLE GMAIL wherein tasks or events are calendared in those applications also installed on the mobile device or through an API that does require some network connectivity but only discloses dosage reminders without necessarily conveying more medical information than necessary to a third party. When the mobile device reads the same optical label again (the schedule already having been constructed) it may assume that such reading is the second dose and so on. Subsequent reads of the optical label may cause the scheduler to confirm visually to the patient that the dosage was indeed taken in the event they review it (noted as strike-through marks on FIG. 12).

Figure 12:
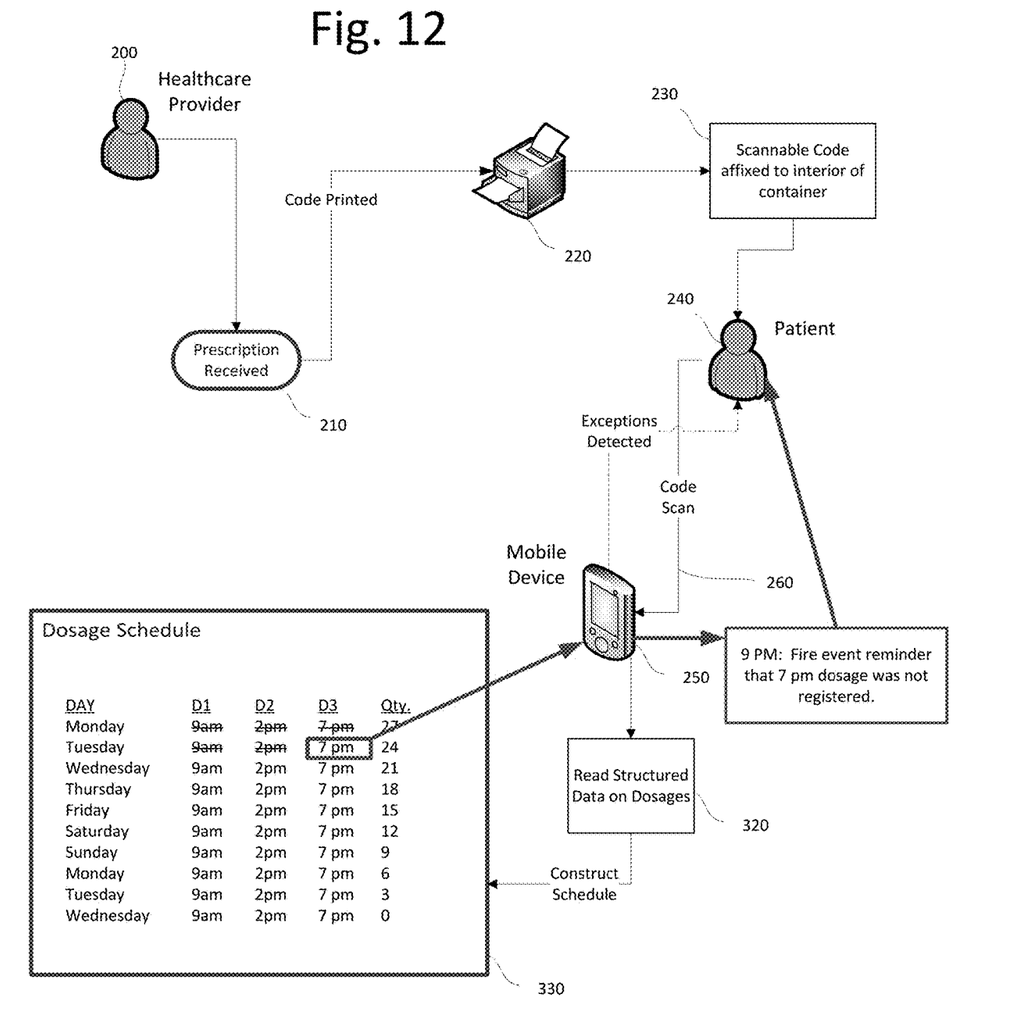
FIG. 12 is a process view of a method of implementing an embodiment of the invention wherein structured data embedded in the optical label builds a dosage schedule on the mobile device software and an exception to the dosage schedule generates an event reminder.

FIG. 12 illustrates an exception to the prescribed schedule wherein the Tuesday, 7 pm dose of the medication was presumably not taken because the optical label was not scanned. In this example, a 2-hour threshold is set for variations in consuming the medication so that at 9 pm, the mobile application software fires an event reminder that the 7 pm dosage was not taken. This could be an audible alarm, screen message, SMS text, phone call or the like. In other embodiments of the invention, as shown in FIG. 10, notification of the exception 310 is transmitted back to healthcare provider 200 to possibly intervene with patient 240.

Figure 13:
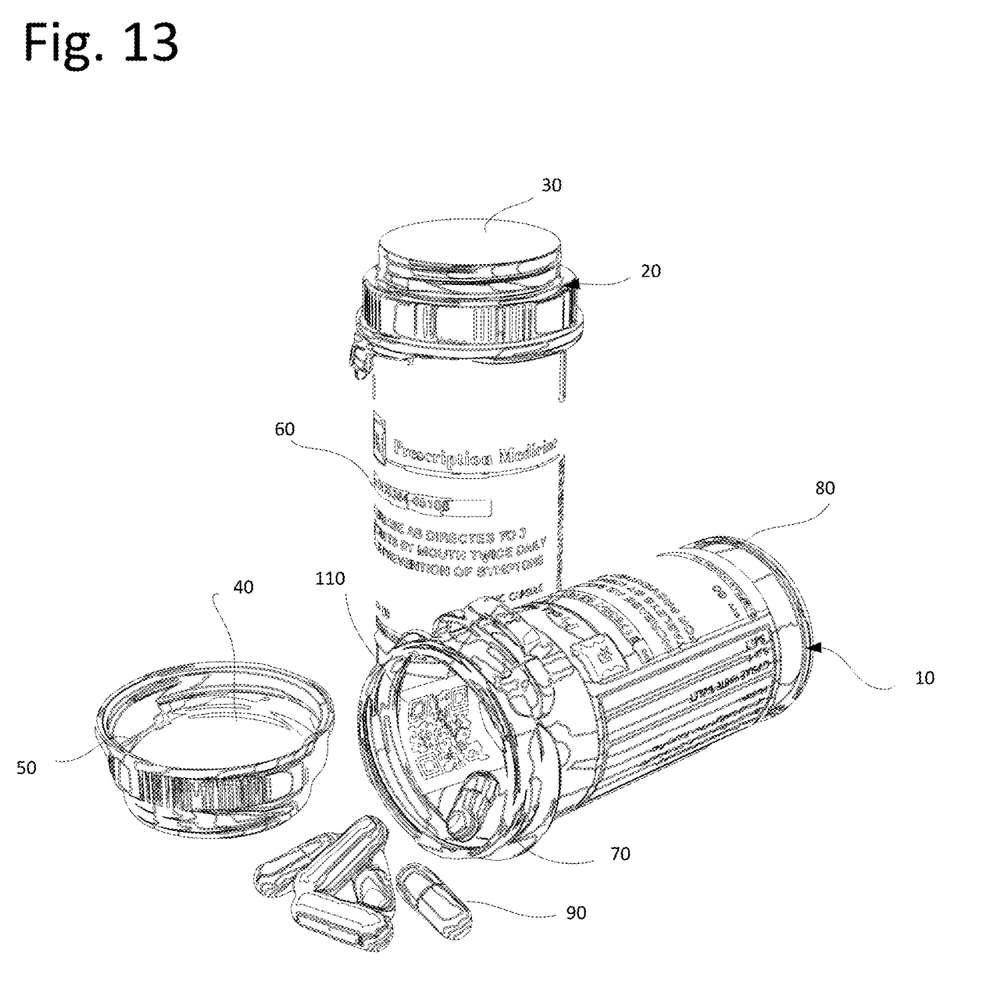
FIG. 13 is a perspective, photo-realistic, front elevated view of an embodiment of the invention wherein the optical label is affixed to the interior sidewall of the prescription container.

FIG. 13 shows an embodiment of the invention wherein optical label 110 is affixed to the interior sidewall of the bottle 10. In this embodiment, one or more pills or capsules may occlude a clear view of the optical label 110. However, a number of 2D matrix-type optical labels support reading with some occlusion and also have error correct features to assure the read is accurate. An advantage of this embodiment is that cap 50 may be placed on a different container of medicine but the optical label 110 remains associated with the correct medication.

Glossary of Claim Terms

Barcode means a machine-readable optical label that contains information about the item to which it is attached.

Dosage means the rate of application of a quantity of medicine.

Medication means a drug used to diagnose, cure, treat, or prevent disease.

Optical Code means a representation of data in a visual, machine-readable form.

Patient means a recipient of health care services.

Portable Electronic Device means a mobile device having a screen, camera function and wireless network connectivity.

Prescription (Rx) means a health-care regiment implemented by a physician or other qualified health care practitioner in the form of instructions that govern the plan of care for an individual patient. For this patent specification, the term refers to a course of a prescription drug typically dispensed from a pharmacist.

QR Code (Quick Response Code) is a trademark of Denso Wave Incorporated for a type of matrix barcode. A QR code consists of black squares arranged in a square grid on a white background, which can be read by an imaging device such as a camera and processed using Reed-Solomon error correction until the image can be appropriately interpreted. The required data is then extracted from patterns that are present in both horizontal and vertical components of the image.

Software Application means software running on top of the operating system of a portable electronic device.

Structured Data means any data that resides in a fixed field within a record or file.

Structured data has the advantage of being easily entered, stored, queried and analyzed.

Timestamp means a sequence of characters or encoded information identifying when a certain event occurred, including the date and time of day.

Uniform Resource Identifier (URI) means a string of characters that unambiguously identifies a particular resource, typically on the Internet.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

What is claimed is:

1. A medication container for electronically tracking medication consumption over a series of timed dosages, the container comprising:
    a body forming the sides of the container, the container having a closed bottom and an open top, a cap is removably affixed to the open top of the body to secure the medication inside the container, the cap has an exterior surface facing away from the body and an interior surface facing the interior of the body; and
    a machine-readable optical code label on the interior surface of the cap, the machine-readable optical code encoding data to schedule a series of timed dosages of the medication, the machine-readable optical code data retrievable by a smartphone software application installed on a smartphone, wherein the optical code label is only electronically readable by the smartphone when the cap is removed from the container.

2. The container of claim 1 wherein the body is semi-opaque.

3. The container of claim 1 wherein the optical code label encodes data for medication prescribed to a patient.

4. The container of claim 1 wherein the optical code is imprinted onto the interior surface of the cap.

5. The container of claim 1 wherein the optical code is printed onto an adhesive label and adhered to the interior surface of the cap.

6. The container of claim 1 wherein the optical code format is selected from the group consisting of AZTEC CODE, DATA MATRIX, DOTCODE, MAXICODE and QR CODE.

7. The container of claim 1 wherein the optical code format is QR CODE and its data density matrix is between 33×33 and 57×57.

8. The container of claim 7 wherein the QR CODE is checked for errors by a Reed-Solomon algorithm.

9. The container of claim 1 further comprising a second optical code on the interior surface of the closed bottom whereby medicine inside the container occludes the second optical code from electronic reading by the smartphone until substantially all the medication in the container is gone.

10. A medication container for electronically tracking medication consumption over a series of timed dosages, the container comprising:
    a body forming the sides of the container, the container having a closed bottom and an open top, a cap is removably affixed to the open top of the body to secure the medication inside the container, the cap has an exterior surface facing away from the body and an interior surface facing the interior of the body, the body has internal sidewalls on the inside of the container; and
    a machine-readable optical code label on the interior sidewalls of the body, the machine-readable optical code encoding data to schedule a series of timed dosages of the medication, the machine-readable optical code data retrievable by a smartphone software application installed on a smartphone, wherein the optical code label is only electronically readable by the smartphone when the cap is removed from the container.

11. The container of claim 10 wherein the body is semi-opaque.

12. The container of claim 10 wherein the optical code label encodes data for medication prescribed to a patient.

13. The container of claim 10 wherein the optical code is imprinted onto the interior surface of the sidewall.

14. The container of claim 10 wherein the optical code is printed onto an adhesive label and adhered to the interior surface of the sidewall.

15. The container of claim 10 wherein the optical code format is selected from the group consisting of AZTEC CODE, DATA MATRIX, DOTCODE, MAXICODE and QR CODE.

16. The container of claim 10 wherein the optical code format is QR CODE and its data density matrix is between 33×33 and 57×57.

17. The container of claim 16 wherein the QR CODE is checked for errors by a Reed-Solomon algorithm.

18. The container of claim 10 further comprising a second optical code on the interior surface of the closed bottom whereby medicine inside the container occludes the second optical code from electronic reading by the smartphone until substantially all the medication in the container is gone.

19. A medication container for electronically tracking medication consumption over a series of timed dosages, the container comprising:
    a semi-opaque body forming the sides of the container, the container having a closed bottom and an open top, a cap is removably affixed to the open top of the body to secure the medication inside the container, the cap has an exterior surface facing away from the body and an interior surface facing the interior of the body;

a machine-readable first optical code label on the interior surface of the cap, the optical code format is QR CODE and its data density matrix is between 33×33 and 57×57, the machine-readable first optical code encoding data to schedule a series of timed dosages of the medication, the machine-readable optical code data retrievable by a smartphone software application installed on a smartphone, wherein the first optical code label is only electronically readable by the smartphone when the cap is removed from the container; and a second optical code on the interior surface of the closed bottom whereby medicine inside the container occludes the second optical code from electronic reading by the smartphone until substantially all the medication in the container is gone wherein scanning of the second optical code by the smartphone is indicative of completion of all medication inside the container.

\* \* \* \* \*